(12) United States Patent
Albarede et al.

(10) Patent No.: US 10,134,569 B1
(45) Date of Patent: Nov. 20, 2018

(54) METHOD AND APPARATUS FOR REAL-TIME MONITORING OF PLASMA CHAMBER WALL CONDITION

(71) Applicant: Lam Research Corporation, Fremont, CA (US)

(72) Inventors: Luc Albarede, Fremont, CA (US); Yassine Kabouzi, Fremont, CA (US); Jorge Luque, Redwood City, CA (US)

(73) Assignee: LAM RESEARCH CORPORATION, Fremont, CA (US)

( * ) Notice: Subject to any disclaimer, the term of this patent is extended or adjusted under 35 U.S.C. 154(b) by 0 days.

(21) Appl. No.: 15/824,061

(22) Filed: Nov. 28, 2017

(51) Int. Cl.
*H01J 37/32* (2006.01)
*G02B 6/02* (2006.01)
*G01N 21/64* (2006.01)

(52) U.S. Cl.
CPC ......... *H01J 37/32917* (2013.01); *G02B 6/02* (2013.01); *G01N 21/648* (2013.01)

(58) Field of Classification Search
CPC .............................. H01J 37/32917; G02B 6/02
USPC ....................................................... 250/252.1
See application file for complete search history.

(56) References Cited

U.S. PATENT DOCUMENTS

| | | | | |
|---|---|---|---|---|
| 2007/0281478 A1* | 12/2007 | Ikegami | ................ | H01J 37/321 438/689 |
| 2010/0214649 A1* | 8/2010 | Burov | ................... | B82Y 20/00 359/334 |
| 2010/0288195 A1* | 11/2010 | Ikegami | ................ | H01J 37/321 118/712 |
| 2013/0120752 A1* | 5/2013 | Lee | .......................... | G02B 6/02 356/445 |
| 2015/0020970 A1* | 1/2015 | Ikegami | ................ | H01J 37/321 156/345.25 |
| 2016/0177449 A1* | 6/2016 | Ohmori | ............. | H01J 37/32917 427/572 |
| 2018/0172728 A1* | 6/2018 | Aksyuk | .................. | G01Q 60/38 |

OTHER PUBLICATIONS

Cennamo, Nunzio et al., "Low Cost Sensors Based on SPR in a Plastic Optical Fiber for Biosensor Implementation," Sensors 2011, 11, 11752-11760; doi:10.3390/s111211752, pub. Dec. 16, 2011. Sensors, ISSN 1424-8220, www.mdpi.com/journal/sensors.

Cottle, Rand, "300mm and 450mm Standard Calibration Wafers," Colleges of Nanoscale Science and Engineering, CNSE-G450C, 15 pages. Undated; estimated date Mar. 2015.

Gonzalez-Cano, Agustin et al., "Plasmonic Sensors Based on Doubly-Deposited Tapered Optical Fibers," Sensors 2014, 14, 4791-4805; doi: 10.3390/s140304791, pub. Mar. 10, 2014.Sensors, ISSN 1424-8220, www.mdpi.com/journal/sensors.

(Continued)

*Primary Examiner* — Marcus Tanningco
*Assistant Examiner* — Gisselle Gutierrez

(57) ABSTRACT

A substrate processing system includes a processing chamber. A pedestal and a showerhead are arranged in the processing chamber. A surface plasmon resonance (SPR) fiber has a central portion disposed in the processing chamber, and opposing ends disposed outside the processing chamber. A light source provides input light at one end of the SPR fiber, and a detector receives output light from the other end of the SPR fiber. Surface plasmon waves and evanescent waves constitute the output light, which is processed and analyzed to determine a condition of the processing chamber.

21 Claims, 12 Drawing Sheets

(56) References Cited

OTHER PUBLICATIONS

Guske, Joshua T. et al., "Infrared surface plasmon resonance of AZO-Ag-AZO sandwich thin films," Optics Express, Oct. 8, 2012, vol. 20, No. 21, pp. 23215-23226.

Jussila, Henri et al., "Surface plasmon resonance for characterization of large-area atomic-layer graphene film," Optica, vol. 3, No. 2, Feb. 2016, pp. 151-158.

Laha, Ranjit et al., "Monitoring plasma treatment of thin films by surface plasmon resonance," Review of Scientific Instruments 85, 035001 (2014); doi: 10.1063/1.4866241, 6 pages. Published online Mar. 3, 2014.

Lee, Kyeong-Seok et al., "Resolution Enhancement in Surface Plasmon Resonance Sensor Based on Waveguide Coupled Mode by Combining a Bimetallic Approach," Sensors 2010, 10, 11390-11399; doi:10.3390/s101211390, pub. Dec. 13, 2010.Sensors, ISSN 1424-8220, www.mdpi.com/journal/sensors.

Takagi, Keiju et al., "Near Infrared Characterization of Hetero-Core Optical Fiber SPR Sensors Coated with Ta2O5 Film and Their Applications," Sensors 2012, 12, 2208-2218; doi:10.3390/s120202208, pub. Feb. 15, 2012.sensors, ISSN 1424-8220, www.mdpi.com/journal/sensors.

Tong, Lianming et al., "Recent Advances in Plasmonic Sensors," Sensors 2014, 14, 7959-7973; doi: 10.3390/s140507959; pub. May 5, 2014.Sensors, ISSN 1424-8220, www.mdpi.com/journal/sensors.

Tsao, Yu-Chia et al., "An In-situ Real-Time Optical Fiber Sensor Based on Surface Plasmon Resonance for Monitoring the Growth of TiO2 Thin Films," Sensors 2013, 13 9513-9521; doi:10.33990/s130709513, pub. Jul. 23, 2013. Sensors, ISSN 1424-8220, www.mdpi.com/journal/sensors.

Vermeeren, Veronique et al., "DNA Sensors with Diamond as a Promising Alternative Transducer Material," Sensors 2009, 9, 5600-5636; doi:10.3390/s90705600, pub. Jul. 14, 2009.Sensors, ISSN 1424-8220, www.mdpi.com/journal/sensors.

* cited by examiner

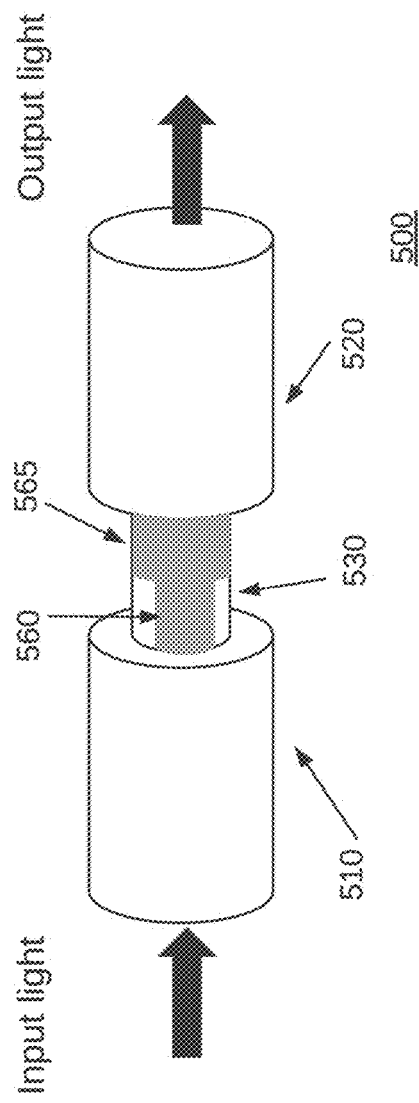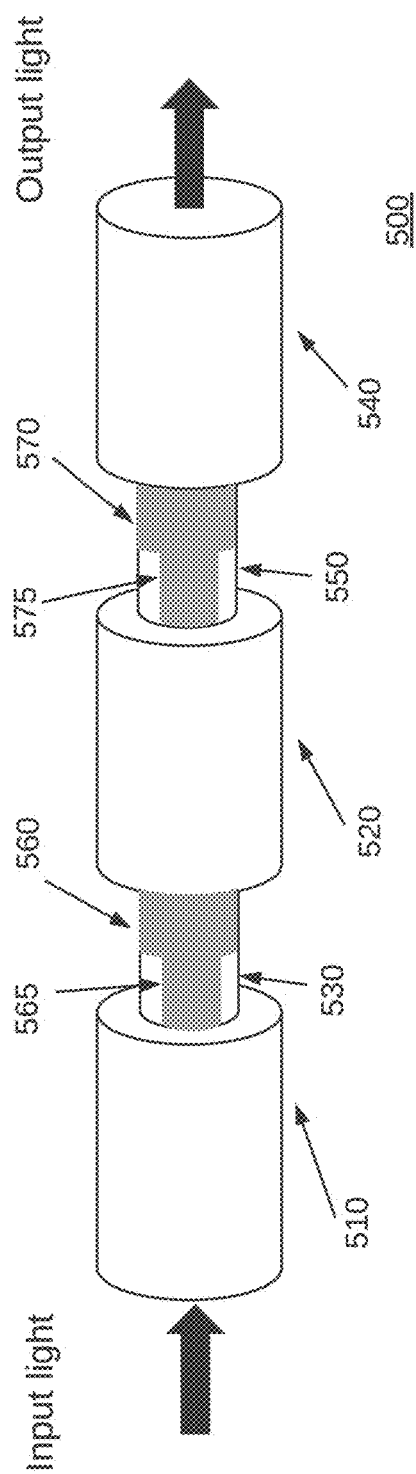
FIG. 7
FIG. 8

METHOD AND APPARATUS FOR REAL-TIME MONITORING OF PLASMA CHAMBER WALL CONDITION

FIELD

The present disclosure relates to substrate processing systems, more particularly to monitoring conditions within processing chambers in substrate processing systems, and yet more particularly to real-time monitoring of conditions within processing chambers in substrate processing systems. Still more particularly, the present disclosure relates to in situ real-time monitoring of conditions within processing chambers in substrate processing systems.

BACKGROUND

The background description provided here is presents the context of the disclosure generally. Work of the presently named inventors, to the extent it is described in this background section, as well as aspects of the description that may not otherwise qualify as prior art at the time of filing, are neither expressly nor impliedly admitted as prior art against the present disclosure.

Substrate processing systems may be used to perform etching and/or other treatment of substrates such as semiconductor wafers. A substrate may be arranged on a pedestal in a processing chamber of the substrate processing system. For example, during etching in a plasma etcher, a gas mixture including one or more precursors is introduced into the processing chamber and plasma is struck to etch the substrate.

It is useful to monitor conditions inside a semiconductor processing chamber, so that processes can be optimized. Conditions inside the chamber may indicate a need for cleaning, for example, or may indicate whether the chamber is sufficiently "seasoned" to be in an optimal condition for wafer fabrication. In one aspect, "seasoning" may refer to a condition of the chamber at a particular time, or it may refer to a steady state condition of the chamber.

It is known to monitor chamber conditions using apparatus positioned outside the chamber. Conditions inside a semiconductor processing chamber are quite hostile to many kinds of equipment. Observation of chamber conditions may be performed through one or more windows in the chamber. It is known, for example, to position a camera or other sensing device at one of the windows to observe conditions inside the chamber.

FIG. 1 shows an example of a substrate processing chamber 500 for performing etching using RF plasma is shown. The substrate processing chamber 500 includes a processing chamber 502 that encloses other components of the substrate processing chamber 500 and contains the RF plasma. The substrate processing chamber 500 includes an upper electrode 504 and a pedestal 506 including a lower electrode 507. An edge coupling ring 503 is supported by the pedestal 506 and is arranged around the substrate 508. One or more actuators 505 may be used to move the edge coupling ring 503. During operation, a substrate 508 is arranged on the pedestal 506 between the upper electrode 504 and the lower electrode 507.

For example only, the upper electrode 504 may include a showerhead 509 that introduces and distributes process gases. The showerhead 509 may include a stem portion including one end connected to a top surface of the processing chamber. A base portion is generally cylindrical and extends radially outwardly from an opposite end of the stem portion at a location that is spaced from the top surface of the processing chamber. A substrate-facing surface or faceplate of the base portion of the showerhead includes a plurality of holes through which process gas or purge gas flows. Alternately, the upper electrode 504 may include a conducting plate and the process gases may be introduced in another manner. The lower electrode 507 may be arranged in a non-conductive pedestal. Alternately, the pedestal 506 may include an electrostatic chuck that includes a conductive plate that acts as the lower electrode 507.

An RF generating system 510 generates and outputs an RF voltage to one of the upper electrode 504 and the lower electrode 507. The other one of the upper electrode 504 and the lower electrode 507 may be DC grounded, AC grounded or floating. For example only, the RF generating system 510 may include an RF voltage generator 511 that generates the RF voltage that is fed by a matching and distribution network 512 to the upper electrode 504 or the lower electrode 507. In other examples, the plasma may be generated inductively or remotely.

A gas delivery system 530 includes one or more gas sources 532-1, 532-2, . . . , and 532-N (collectively gas sources 532), where N is an integer greater than zero. The gas sources supply one or more precursors and mixtures thereof. The gas sources may also supply purge gas. Vaporized precursor may also be used. The gas sources 532 are connected by valves 534-1, 534-2, . . . , and 534-N (collectively valves 534) and mass flow controllers 536-1, 536-2, . . . , and 536-N (collectively mass flow controllers 536) to a manifold 540. An output of the manifold 540 is fed to the processing chamber 502. For example only, the output of the manifold 540 is fed to the showerhead 509.

A heater 542 may be connected to a heater coil (not shown) arranged in the pedestal 506. The heater 542 may be used to control a temperature of the pedestal 506 and the substrate 508. A valve 550 and pump 552 may be used to evacuate reactants from the processing chamber 502. A controller 560 may be used to control components of the substrate processing chamber 500. The controller 560 may also be used to control the actuator 505 to adjust a position of one or more portions of the edge coupling ring 503.

A robot 570 and a sensor 572 may be used to measure erosion of the edge coupling ring. In some examples, the sensor 572 may include a depth gauge. The robot 570 may move the depth gauge in contact with the edge coupling ring to measure erosion. Alternately, a laser interferometer (with or without the robot 570) may be used to measure erosion without direct contact. The robot 570 may be omitted if the laser interferometer can be positioned with a direct line of sight to the edge coupling ring.

FIG. 2A shows an example of an approach to detecting conditions at a wall of a chamber. For ease of description, many of the elements in FIG. 1 are omitted here. In FIG. 2A, a semiconductor processing chamber 100 includes a pedestal 110, on which an electrostatic chuck (ESC) 115 may be mounted. A wafer or substrate 120 is positioned on the ESC.

At the top of the chamber, a conduit 130 passes plasma to showerhead 135, which distributes the plasma in the chamber. As substrates get processed, there can be buildup on the walls of the chamber. A detection apparatus includes a light source 170 and a camera/detector 175. The light source 170 shines light through a first opening 180 onto a mirror 165 at an opposite end of the chamber. Camera/detector 175 picks up light reflected from mirror 165 through a second opening 185. Controller 160 communicates with camera/detector 175 to operate the camera and to receive output from the camera/detector. Controller 160 also controls operation of light source 170. Shutters 190, 195 respectively operate to cover windows 180, 185 when the detection apparatus is not in operation, or the chamber is not in use.

Controller 160 may process data from the camera/detector 175, using known signal processing algorithms and/or other computational techniques, to obtain information about wall conditions in chamber 100. Alternatively, controller 160 may pass obtained data to other processing apparatus (not shown here for ease of description) for that purpose.

In operation, whatever builds up on the chamber walls also builds up on mirror 165, thereby affecting the mirror's ability to reflect light from source 170 to camera/detector 175. Controller 160 takes the amount of light that camera/detector 175 receives as reflected from mirror 165, and given the light that light source 170 outputs, and the material being deposited on the walls of the chamber (and therefore on the mirror 165), computes/estimates the amount of buildup on the mirror.

There also will be buildup on the windows 180, 185 through which the transmitted light enters, and the reflected light leaves. As an approximation, to make calculations easier it may be assumed that the amount of buildup on the windows is the same as the amount of buildup on the mirror.

FIG. 2B shows a variant of the setup in FIG. 2A, in which the camera/detector 175 and the window 185 are positioned on an opposite side of the chamber from their positions in the system of FIG. 2A. The FIG. 2B approach removes the requirement for a mirror inside chamber 100. Again, as an approximation, for ease of calculation, it may be assumed that the amount of buildup on window 185 will be the same as on window 180.

There are various issues associated with the FIG. 2A apparatus and detection approach. One issue with respect to the FIG. 2A system is that the light from source 170 has to be tightly focused onto mirror 165, so that what comes back from mirror 165 is a reliable indication of the light that the source 170 is providing. The light source 170 may be a laser or other source of coherent light which enables tight focusing on mirror 165. Movement of any of several elements in FIG. 2 can affect the ability of camera/detector 175 to receive reflected light properly. For example, movement of the light source 170 outside the chamber, or movement of the mirror 165 inside the chamber, or movement of the chamber itself may require refocusing of the light source 170 onto the mirror 165. In addition, movement of the mirror 165 or chamber containing the mirror may require repositioning of the camera/detector 175, as the angle of reflection from the mirror 165 may change. As a result of all of these possibilities, frequent repositioning/refocusing of source 170 and/or camera/detector 175 may be necessary. Another issue is that, just as there is buildup on mirror 165, there also will be buildup on windows 180, 185, thereby affecting not only the amount of light that the source 170 will provide, but also the amount that camera/detector 175 will detect. While it may be assumed that buildup of material on chamber walls (and hence on the mirror and windows) is uniform, depending on the process being utilized, that might not be the case. As a result, given the different location of the mirror 165 from the windows 180, 185, there may be different amounts of buildup in the different locations, making it difficult to provide a reliable estimate of buildup on the windows.

The FIG. 2B approach eliminates detection and accuracy issues associated with the mirror 165. However, because the windows 180, 185 are on opposite sides of the chamber, the FIG. 2B approach retains the issue of differential amounts of buildup in different parts of the chamber. In addition, by using direct transmission of light instead of reflected transmission, the FIG. 2B approach ameliorates focusing issues associated with movement of light source 170, camera/detector 175, or the chamber 100. However, those focusing issues will persist to some degree.

There have been efforts to provide detection equipment inside the chamber, to provide more direct measurement. A significant difficulty with that approach is the hostile environment that plasma provides to that equipment.

It would be useful to have more accurate monitoring of chamber conditions.

SUMMARY

A substrate processing system includes a processing chamber having a chamber wall, and a pedestal arranged in the processing chamber to hold a substrate for processing. The substrate processing system includes a showerhead arranged in the processing chamber to distribute plasma in the chamber. The substrate processing further includes a detector system configured to detect a condition of the chamber wall. The detector system includes a surface plasmon resonance (SPR) fiber having a first end and a second end positioned outside the processing chamber, and an inner portion of the SPR fiber positioned inside the processing chamber. A light source provides input light to the first end of the first SPR fiber. A controller is configured to control an amount of light provided to the first end of the SPR fiber, and to receive light at the second end of the SPR fiber as output light. The controller analyzes the input light and the output light to determine the condition of the chamber wall.

In one aspect, on the portion of the SPR fiber inside the chamber, one or more portions of cladding on the fiber may be removed to provide one or more openings. The openings are filled with inserts constituted to provide both surface plasmon waves and evanescent waves whose characteristics are used in determining conditions in the chamber.

In one feature, the openings in the SPR fiber may be close enough together, yet far enough apart to ascertain conditions in different portions of the chamber. In another feature, the openings in the SPR fiber may be far enough apart to be spaced around the chamber, to ascertain conditions on opposite sides of the chamber.

In one feature, multiple SPR fibers may be provided in different parts of the chamber. In another feature, an SPR fiber may be used as a reference, disposed outside of the chamber, with the controller using output light from the reference SPR fiber to compare with output light from the SPR fiber in the chamber, thereby to determine a baseline for ascertaining the condition of the chamber wall.

In other features, the input light may be a laser, such as a quantum cascade laser (QCL), which provides light transmission in an appropriate infrared (IR) band. In other features, the laser may be a type of distributed feedback laser (DFB), which provides light transmission in a narrower wavelength range, even to a specific wavelength.

A method for measuring a condition of an interior wall of a chamber in a substrate processing system includes measuring a surface plasmon wave and an evanescent wave generated within the chamber. In one aspect, those waves may be generated using the SPR fiber and associated apparatus described earlier in this section. The resulting measurements may be used to ascertain a condition of walls of the chamber.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 7 is an explanatory diagram showing light passing through an SPR fiber with one opening and a coating over an exposed fiber portion according to one aspect of the present disclosure;

FIG. 8 is an explanatory diagram showing light passing through an SPR fiber with two openings and coating over exposed fiber portions according to one aspect of the present disclosure;

In the drawings, reference numbers may be reused to identify similar and/or identical elements.

DETAILED DESCRIPTION

Figure 3A:
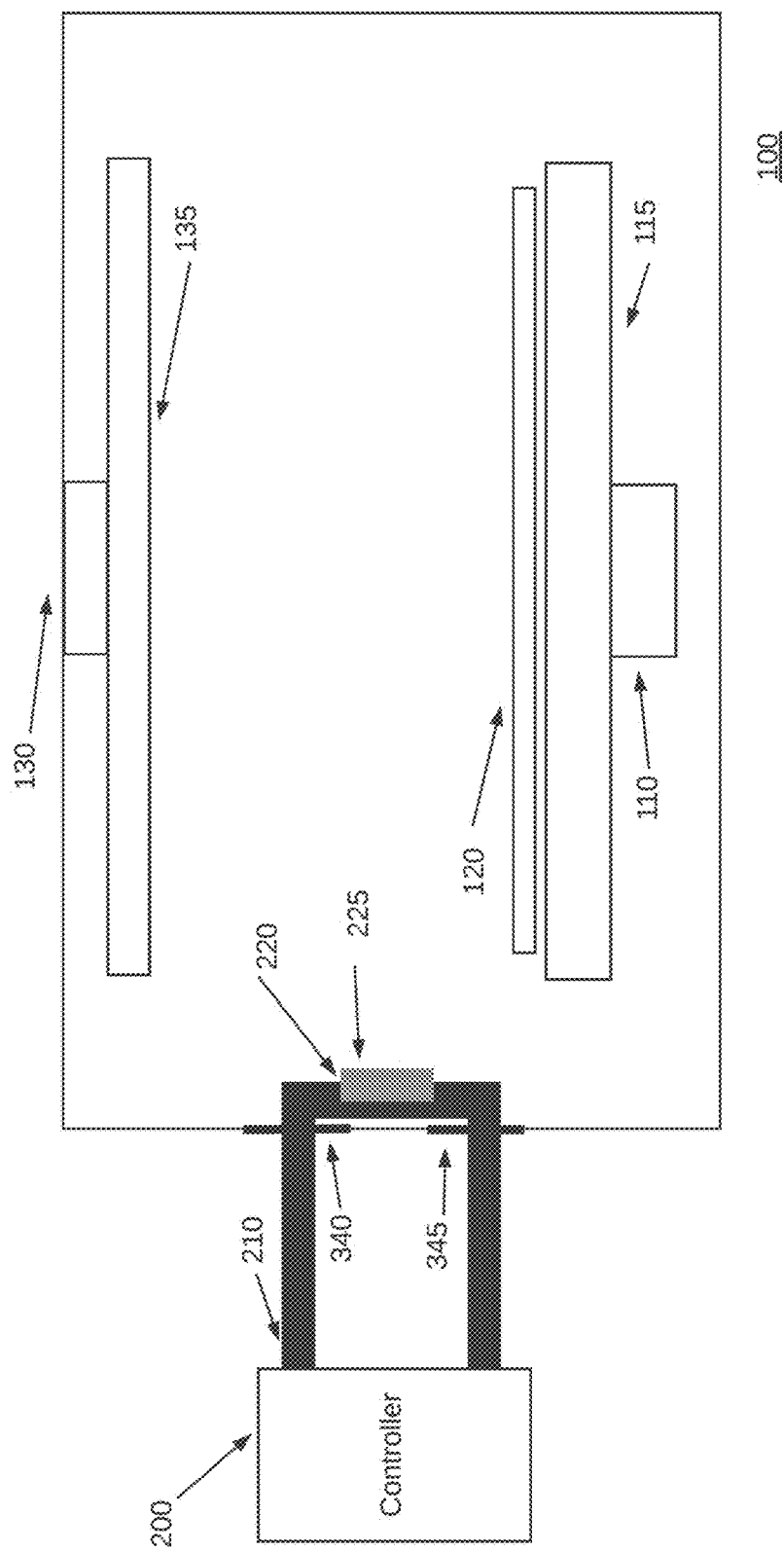
FIG. 3A is a functional block diagram of an example of a substrate processing chamber including a pedestal and a showerhead assembly, and an example of apparatus for detecting conditions inside the chamber according to one aspect of the present disclosure.

Referring now to FIG. 3A, features of SPR fiber placement in a substrate processing chamber, and associated apparatus to enable the fiber's use as a detector for conditions inside the chamber, now will be described. This part of the description focuses on the detector and detection method according to features of the present disclosure, enabling direct measurement of internal chamber conditions. Details of various elements of the processing chamber, including the ESC, for the sake of brevity and clarity will not be repeated here.

Figure 1:
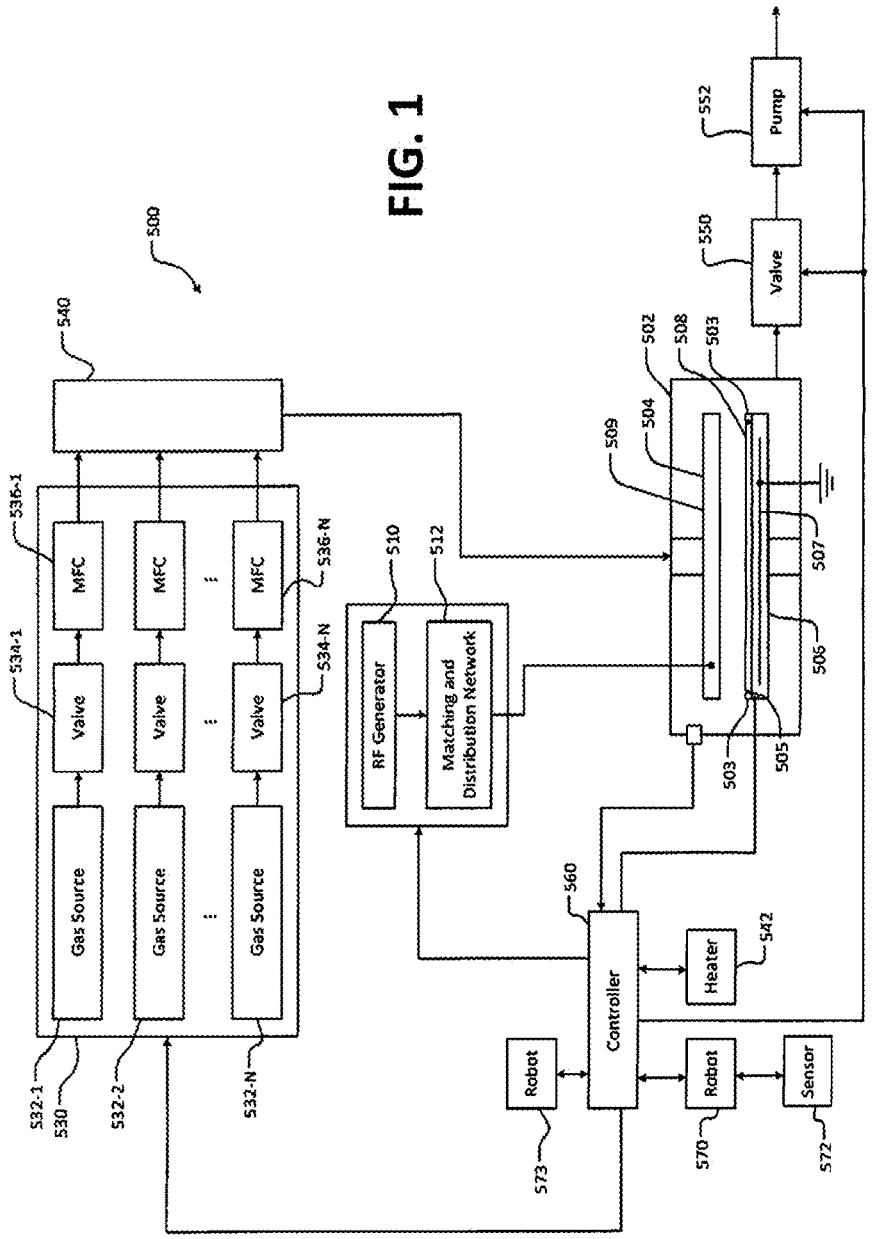
FIG. 1 is a functional block diagram of an example of a substrate processing chamber including a pedestal and a showerhead assembly.
Figure 2A:
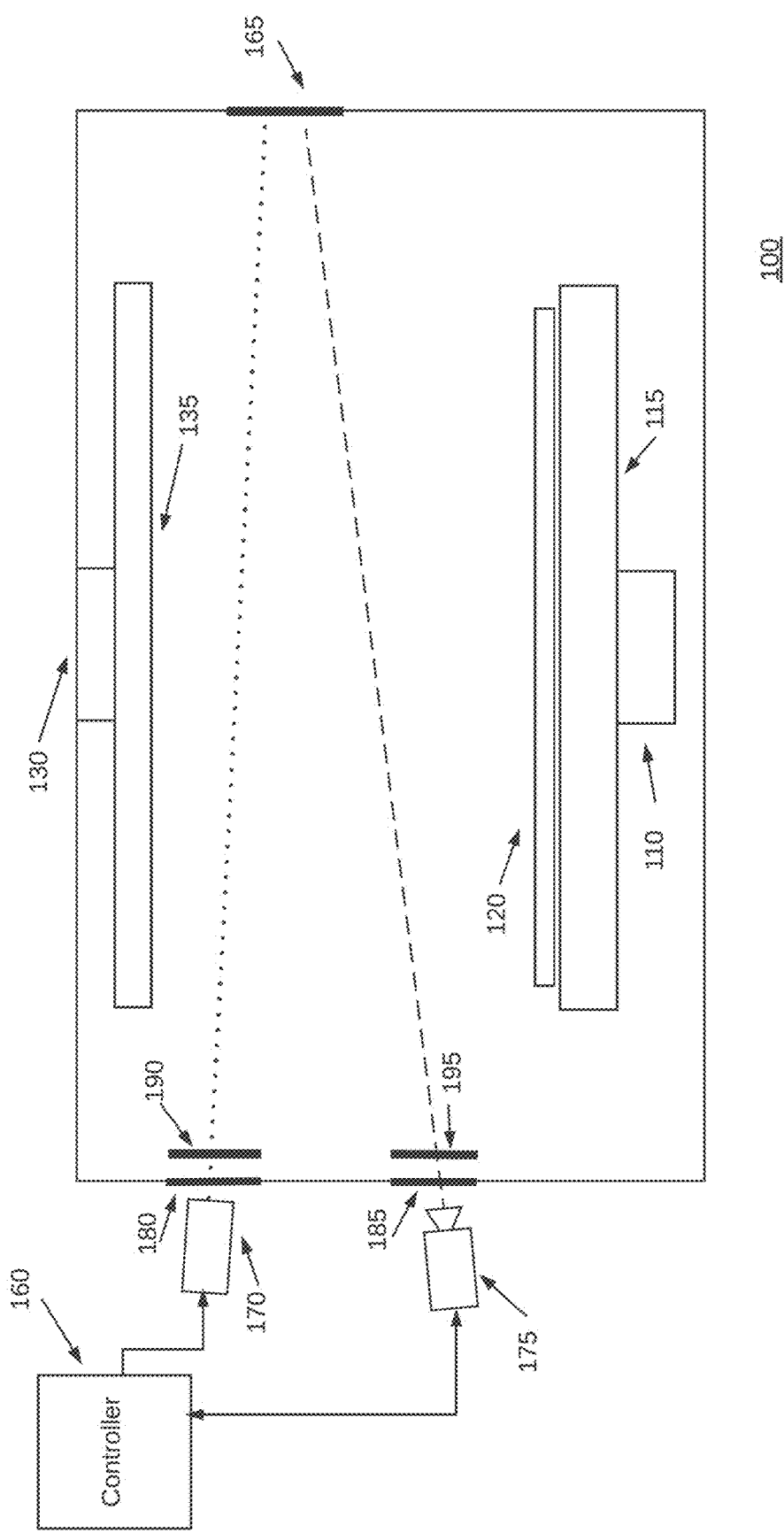
FIG. 2A is a functional block diagram of an example of a substrate processing chamber including a pedestal and a showerhead assembly, and an example of apparatus for detecting conditions inside the chamber according to one aspect of the present disclosure.
Figure 2B:
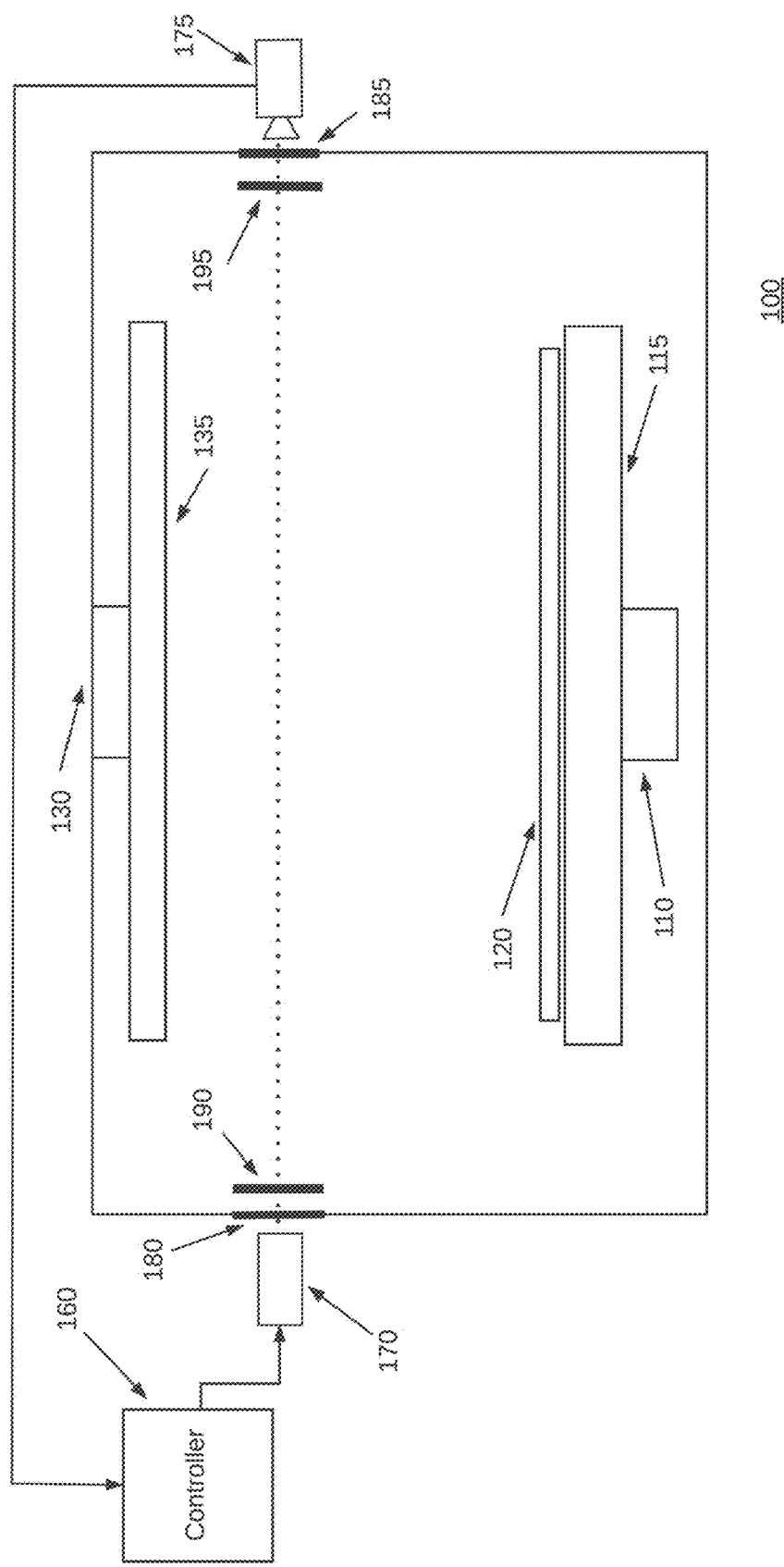
FIG. 2B is a functional block diagram of an example of a substrate processing chamber including a pedestal and a showerhead assembly, and an example of apparatus for detecting conditions inside the chamber according to one aspect of the present disclosure.

In FIG. 3A, certain elements that are the same as those in FIGS. 2A and 2B bear the same reference numbers. FIG. 3A has a controller 200 which includes, in one aspect, a light source, a light detector, and a processor. An SPR fiber 210 extends through feedthroughs 340, 345. Such feedthroughs are well known to ordinarily skilled artisans, and so will not be detailed here. One end of SPR fiber 210 receives input light from a light source in controller 200, and provides output light to a light detector in controller 200. An SPR fiber such as fiber 210 has an opening 220 in an outer cladding to expose the fiber within. As will be explained, materials placed over the opening 220 in SPR fiber 210 will affect the passage of light from an input end to an output end of the fiber in a measurable way, according to known physical and optical characteristics of the fiber and the exposure of an unclad section of the fiber to conditions inside chamber 100.

FIG. 3A shows SPR fiber 210 having an exposed portion in chamber 100. In addition, FIG. 3A shows separate feedthroughs 340, 345 receiving respective ends of SPR fiber 210. In one aspect, the ends of a particular SPR fiber may pass through the same feedthrough.

Insert 225, which will be described in more detail herein, covers the exposed fiber, to protect it from conditions inside the chamber 100. Insert 225 also has known light transmission and reflection characteristics. When light passes through the SPR fiber 210, the insert 225 also will affect the passage of light from the input end to the output end of the fiber, in a known way.

To ready the detection system for operation, the light detection and processing system acquires information about how the SPR fiber 210 will handle light transmission and reception in the chamber 100. Before running the substrate processing system, spectral data for the SPR fiber 210 in the chamber 100 is acquired to allow identification of a baseline. The baseline may be identified in a couple of ways. In one aspect, the baseline may be identified first by taking light measurements using a purely uncovered, uncladded opening of the SPR fiber 210 in the chamber 100, followed by taking the same measurements after insert 225 is added. In another aspect, the baseline may be identified by taking only measurements of the SPR fiber 210 with the insert 225. In another aspect, a baseline may be identified by measuring light passing through a fully covered, cladded fiber.

After completing the baseline identification, additional reference measurements may be obtained. For example, the substrate processing system may be run with coupons placed on the ESC. As the substrate processing system operates, deposition material will accumulate on various exposed parts in the chamber 100, including on the SPR fiber 210. Different deposition materials also have different light spectral characteristics which identify them uniquely. Light measurements may be taken as particular deposition materials are introduced into the chamber 100 and deposited onto the coupons. Deposition may occur for a period of time, during which the thickness of deposited material on the SPR fiber 210 will increase. Periodic or continual measurements of light transmitted through SPR fiber 210 are taken, and are correlated to deposition thicknesses. Alternatively, the chamber 100 may be opened periodically, and thickness measurements taken directly. Thickness measurements for materials deposited on the chamber walls also may be taken directly, and compared with deposition thicknesses measured on insert 225 in SPR fiber 210.

Figure 3B:
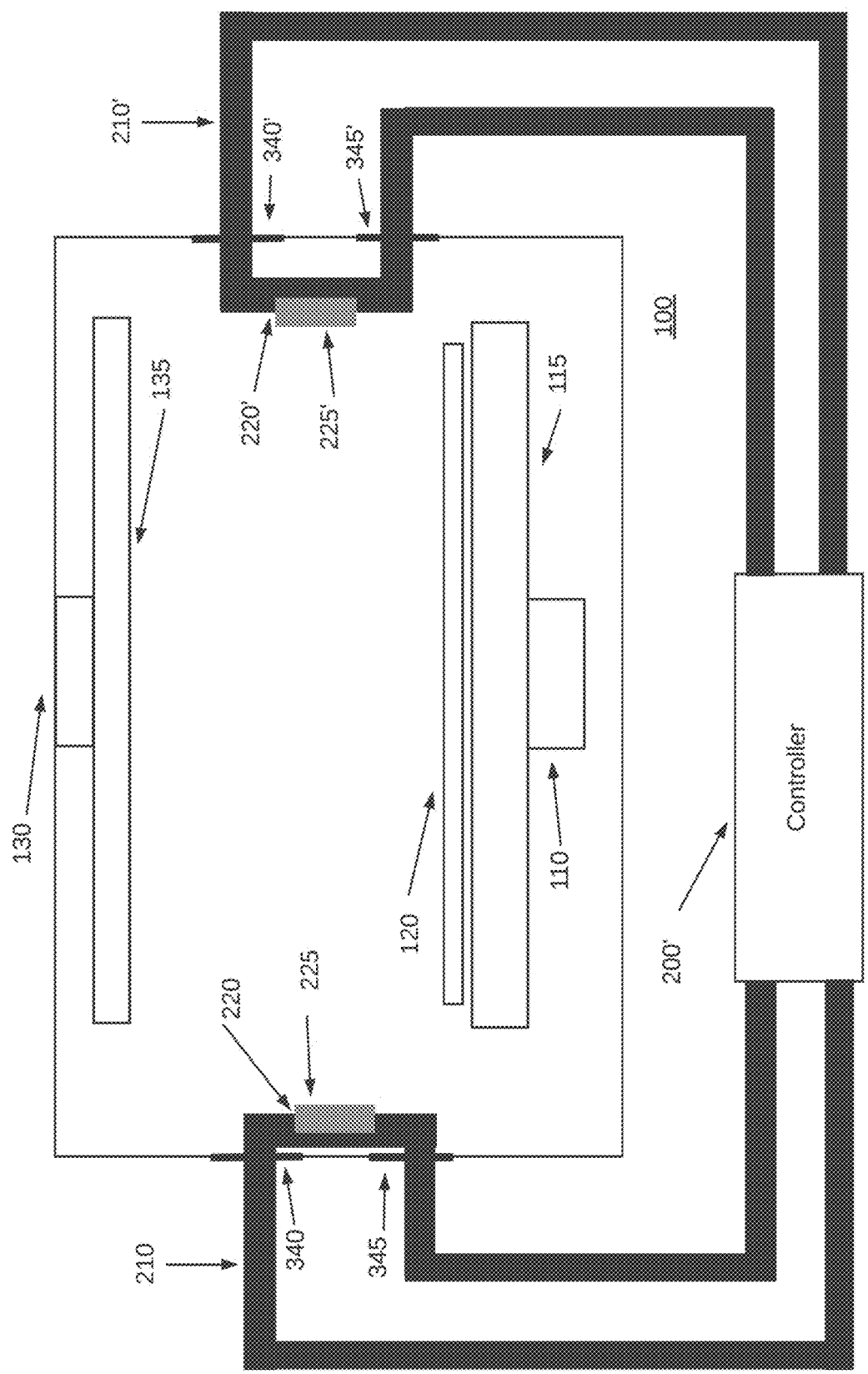
FIG. 3B is a functional block diagram of an example of a substrate processing chamber including a pedestal and a showerhead assembly, and an example of apparatus for detecting conditions inside the chamber according to one aspect of the present disclosure.

In one aspect, multiple fibers may be disposed in multiple locations around chamber 100, with corresponding feedthroughs provided for respective ends of each fiber. FIG. 3B shows a second SPR fiber arrangement on an opposite side of the chamber from the first SPR fiber arrangement which FIG. 3A shows.

FIG. 3B has a controller 200' which includes, in one aspect, a light source, a light detector, and a processor. In addition to an SPR fiber 210 extending through feedthroughs 340, 345, another SPR fiber 210' extends through feedthroughs 340', 345'. SPR fiber 210 has been discussed above, and for brevity will not be discussed further here. One end of SPR fiber 210' receives input light from a light source in controller 200', and provides output light to a light detector in controller 200'. An SPR fiber such as fiber 210' has an opening 220' in an outer cladding to expose the fiber within. As will be explained, materials placed over the opening 220' in SPR fiber 210' will affect the passage of light from an input end to an output end of the fiber in a measurable way, according to known physical and optical characteristics of the fiber and the exposure of an unclad section of the fiber to conditions inside chamber 100.

FIG. 3B shows SPR fiber 210' having an exposed portion in chamber 100. In addition, FIG. 3B shows separate feedthroughs 340', 345' receiving respective ends of SPR fiber 210'. In one aspect, the ends of a particular SPR fiber may pass through the same feedthrough.

Insert 225' covers the exposed fiber, to protect it from conditions inside the chamber 100. Insert 225' also has known light transmission and reflection characteristics. When light passes through the SPR fiber 210', the insert 225' also will affect the passage of light from the input end to the output end of the fiber, in a known way.

Other aspects of the system shown in FIG. 3B operate equivalently to the system shown in FIG. 3A.

Figure 4:
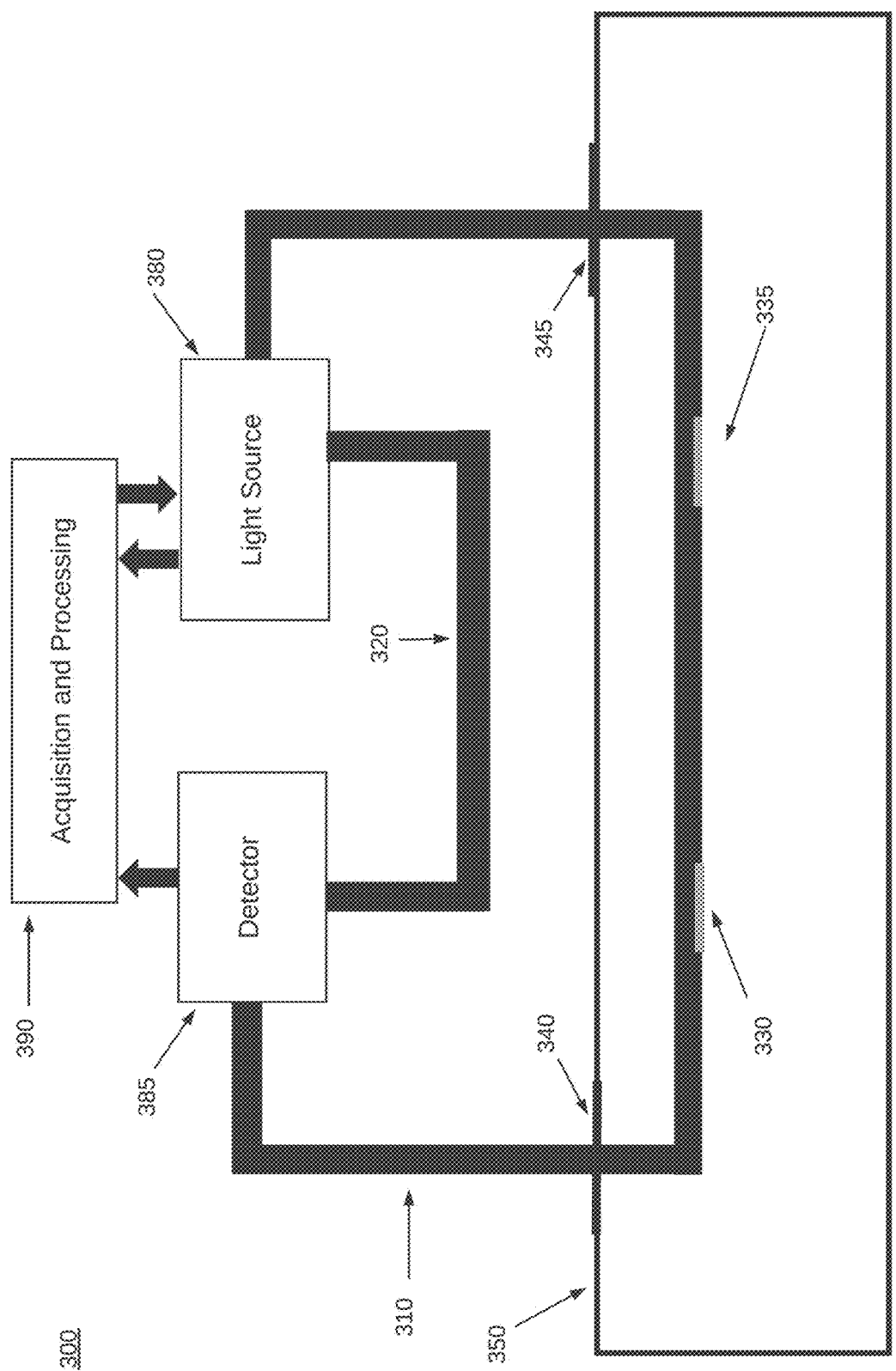
FIG. 4 is a functional block diagram of an example of a substrate processing chamber including a pedestal and a showerhead assembly, and an example of apparatus for detecting conditions inside the chamber according to another aspect of the present disclosure.

FIG. 4 shows a detection system as used in a substrate processing chamber in accordance with an aspect of the present disclosure. For ease of discussion, other elements of the processing chamber have been removed. An SPR fiber with two openings, with the fiber portion with the openings placed inside a substrate processing chamber, and a reference fiber outside the chamber, with no such openings, are shown symbolically, are not intended to show actual positioning inside and outside the chamber, and are not drawn to scale.

Looking more closely at FIG. 4, a substrate processing system 300 has a chamber 350 with feedthroughs 340, 345. An SPR fiber 310 goes through the feedthroughs 340, 345. The SPR fiber 310 has exposed openings with inserts 330, 335 disposed thereon. Acquisition/processing apparatus 390 communicates with light source 380, which passes light through one end of SPR fiber 310. Detector 385 receives light through the other end of SPR fiber 310, and passes information about the detected light to acquisition/processing apparatus 390.

In one aspect, a second or reference SPR fiber 320 may pass light from light source 380 to detector 385. The second SPR fiber 320, which has the same core and cladding as SPR fiber 310, has no openings, and is disposed outside of chamber 350, may act as a reference for the information received from SPR fiber 310 when it passes light from light source 380 to detector 385. For example, the second SPR fiber 320 may provide baseline data for comparison with data acquired from processing light through SPR fiber 310, when walls of chamber 350 are clean and/or before the substrate processing system 300 begins or resumes operation. As the system 300 is operated and material builds up on walls of chamber 350, the baseline data also may be compared to subsequent data acquired from processing light through SPR fiber 310. In one aspect, in addition to looking at differences between the baseline data and the pre- and/or inter-operational data from the SPR fiber 310, looking at differences between the pre- and/or inter-operational data from the SPR fiber 310 and mid-operational data from the SPR fiber 310 may provide additional information about a condition of the walls of chamber 350.

Figure 5:
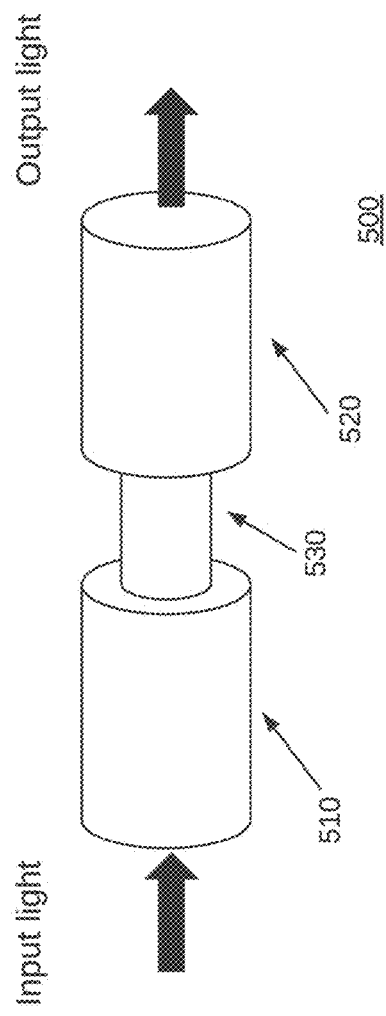
FIG. 5 is an explanatory diagram showing light passing through an SPR fiber with one opening according to one aspect of the present disclosure.
Figure 6:
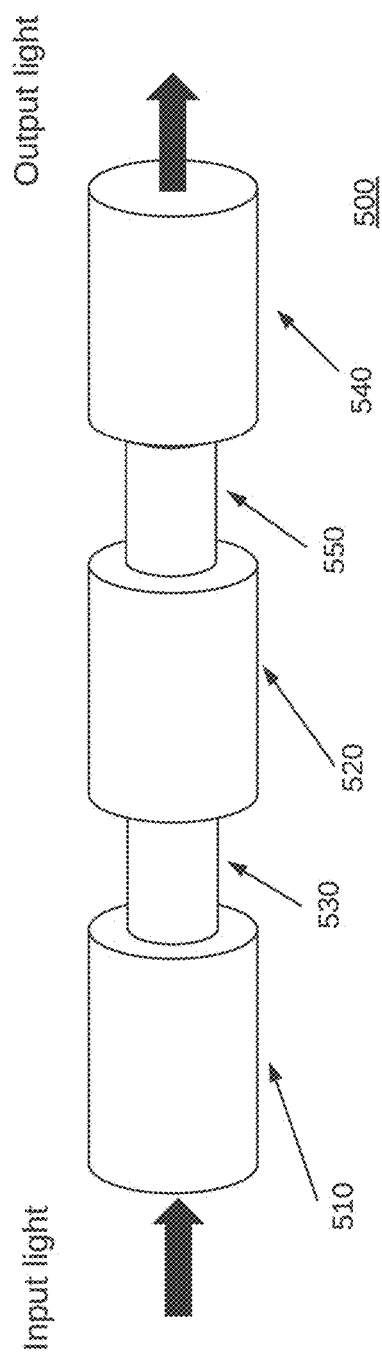
FIG. 6 is an explanatory diagram showing light passing through an SPR fiber with two openings according to one aspect of the present disclosure.

Looking more closely now at the SPR fiber that forms part of the detection system according to aspects of the present disclosure, FIGS. 5 and 6 show opening portions of an SPR fiber 500. FIG. 5 shows a single exposed portion 530 in the fiber 500 between cladding portions 510 and 520 which cover the fiber core. FIG. 6 shows two exposed portions 530, 550. Exposed portion 530 is between cladding portions 510 and 520, and exposed portion 550 is between cladding portions 520 and 540.

The exposed portions 530, 550 in FIG. 6 are shown symbolically. Spacing between the exposed portions 530, 550 may be determined as appropriate to facilitate detection of material buildup in different parts of a substrate processing chamber. Also, according to an aspect of the present disclosure, there may be more than two exposed portions 530, 550 in SPR fiber 500.

FIGS. 7 and 8 show similar views to FIGS. 5 and 6, but additionally show a thin layer of metal film disposed over exposed portion 530. Film portion 560 extends all the way around the exposed portion 530. Film portion 565 extends part way around the exposed portion 530, to show both exposed and covered portions of the fiber 500. The film portions 560, 565 may be made of gold, as often is the case with SPR fibers. Gold is not plasma resistant, and can contaminate the chamber when exposed to plasma etch. Accordingly, as will be discussed below with respect to FIGS. 9 and 10, other materials disposed over the film portions nearest the exposed portion will be more plasma resistant, and will avoid the contamination issue.

As with FIG. 6. the exposed portions in FIG. 8 are shown symbolically. Spacing between the exposed portions 530, 550 may be determined as appropriate to facilitate detection of material buildup in different parts of a substrate processing chamber.

Figure 9:
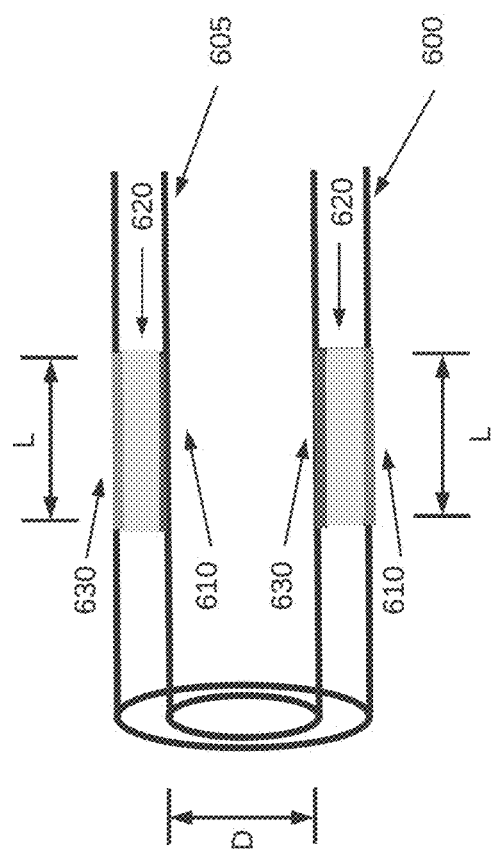
FIG. 9 is a diagram of a portion of an SPR fiber with one opening, and materials covering the opening.
Figure 10:
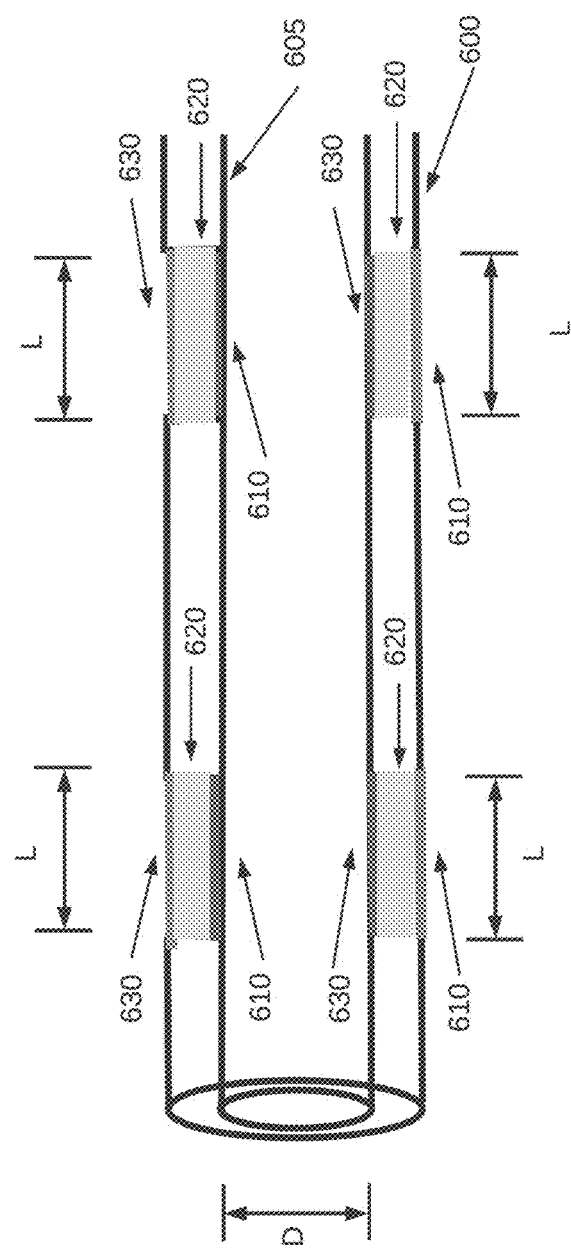
FIG. 10 is a diagram of a portion of an SPR fiber with two openings, and materials covering the openings.

Similarly to FIGS. 7 and 8, FIGS. 9 and 10 show portions of SPR fibers with one opening and two openings, respectively. As with FIGS. 6 and 8, the openings in FIG. 10 are depicted symbolically in terms of their degree of separation, and are not drawn to scale.

In FIGS. 9 and 10, an SPR fiber 600 has an internal portion 605 with diameter D. In one aspect, the internal portion 605 is constituted to provide total internal reflection, or TIR, up to a certain angle of incidence which depends, among other things, on the diameter D and the index of refraction of the internal portion 605. Looking more closely at FIG. 9, a metal layer 610 is deposited over the exposed internal portion 605. In one aspect, the metal layer 610 is made of gold. Dielectric material 620 is provided over the metal layer 610, and a dielectric sensing layer 630 is provided over the dielectric material 620. The layers 610, 620, and 630 together correspond to the insert 225, 330, and 335 in FIGS. 3 and 4. In FIGS. 9 and 10, the internal portion 605 is exposed around its entire circumference, though that is not essential for operation.

Because, as noted earlier, metal such as gold may not be resistant to plasma etch, the gold can contaminate the chamber. As a result, it is necessary to provide a layer over the layer 610 (a metal layer which may be gold) which has high reflectivity, sufficient etch-resistance, and an optical index which allows the evanescent wave. Materials such as $MgF_2$ and $BaF_2$ may be suitable to protect a gold layer from HF, HCl, and/or fluorine reactive gases. When $MgF_2$ or $BaF_2$ is used, aluminum may be used in place of gold. Chromium (Cr) also is plasma-resistant, and may be used instead of gold, with or without a $MgF_2$ or $BaF_2$ coating. In one aspect, the dielectric material 620 also will have favorable plasma-resistant characteristics.

In one aspect, the layer 610 may be made of gold, and may be 100 nm thick. The layer 620 or 630, while shown in the Figures to be thicker or the same thickness, may be thinner, for example, 1 to 5 nm.

Figure 11:
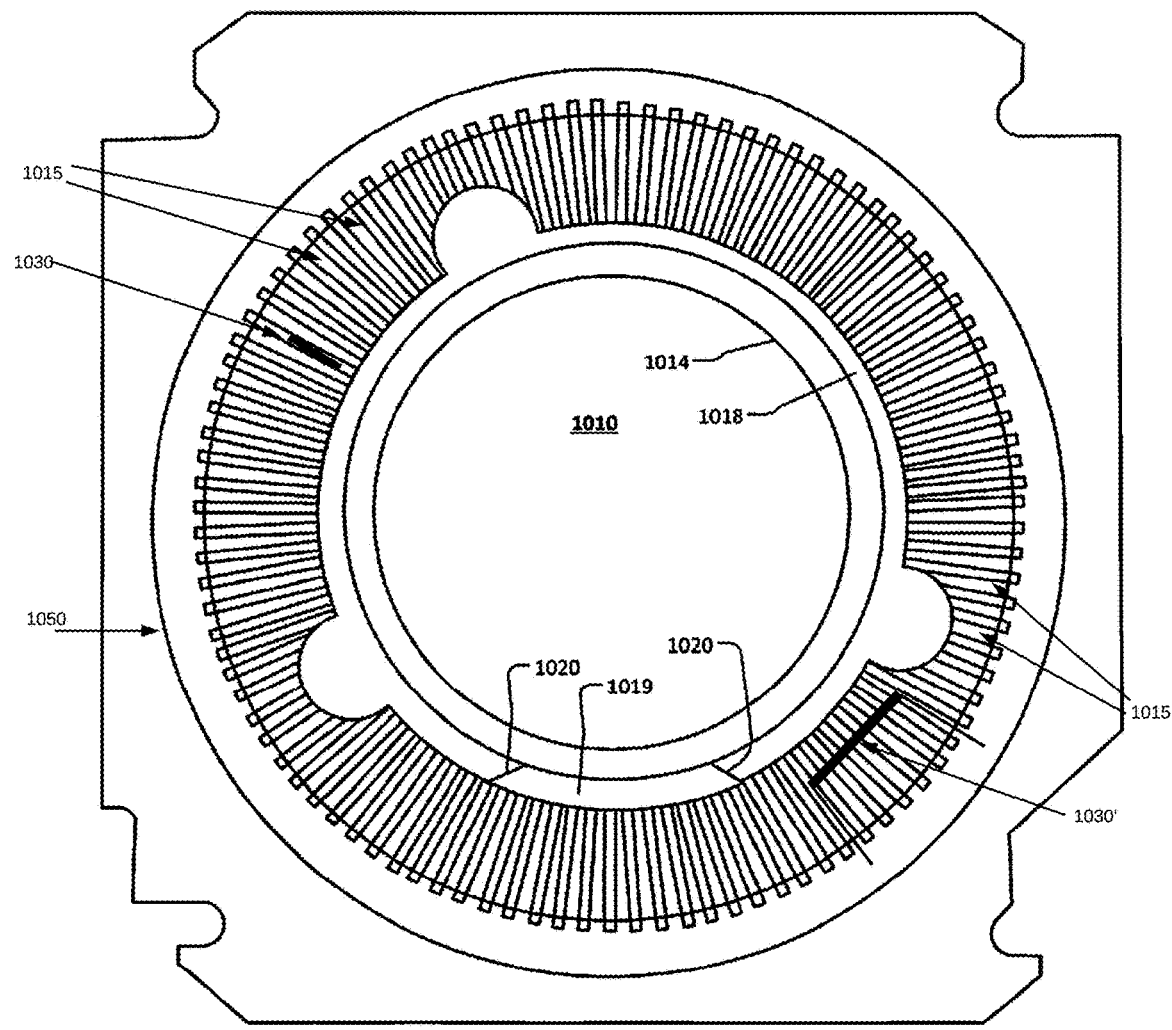
FIG. 11 is a plan view of a liner in a substrate processing chamber according to one aspect.

With respect to SPR fiber placement in a substrate processing chamber, in one aspect, referring to FIG. 11, a liner 1012 has a plurality of openings 1015. In one aspect, liner 1012 is made of yttrium. FIG. 11 shows an SPR fiber 1030 which is positioned in an interior of liner 1012. Ends of the SPR fiber 1030 extend through an opening 1015 to an exterior of liner 1012. In one aspect, the fiber ends extending outside of liner 1012 are inserted into an yttrium tube (not shown) to protect them from etchants in the substrate processing chamber.

In one aspect, much of the SPR fiber 1030 runs behind the liner 1012, with the active or sensing area inside the liner 1012 being aligned with one of the openings 1015 which may be used for high gas conductance. In this manner, much of the length of the SPR fiber 1030 may be protected from direct plasma. In FIG. 11, different lengths of SPR fibers 1030, 1030' are shown within liner 1012. To protect the fibers 1030, 1030' from direct plasma, only the exposed (cladding removed) portions of fibers 1030, 1030' may be positioned within the liner 1012. In one aspect, an SPR fiber 1030' may be positioned horizontally, rather than vertically, in the chamber, in which case the SPR fiber 1030' would extend through two of the openings 1015, as shown.

Figure 12:
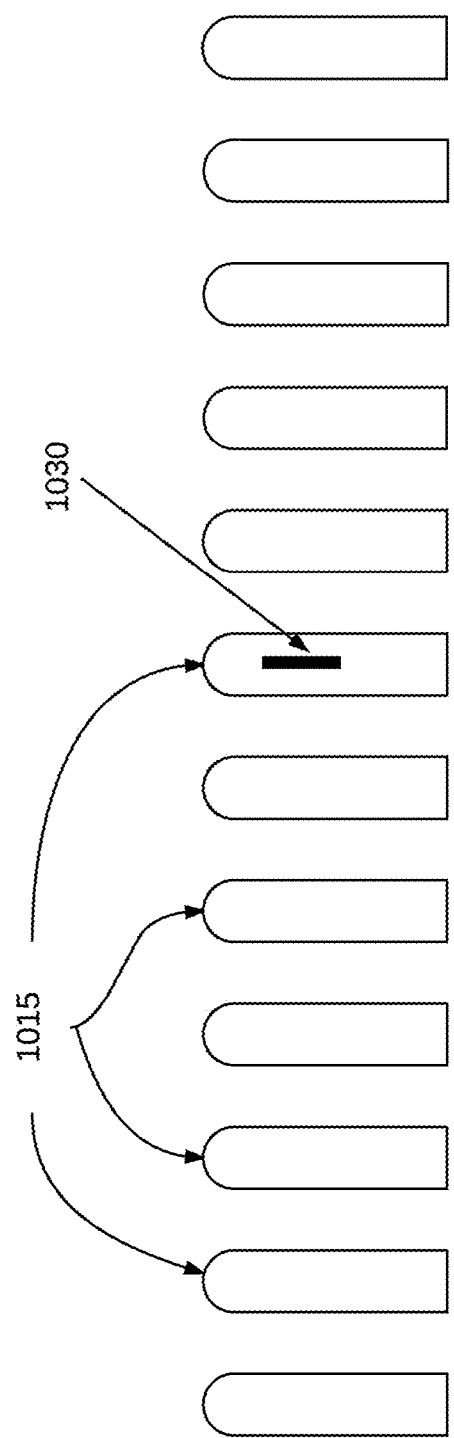
FIG. 12 is an enlarged view of portions of the liner depicted in FIG. 11.

FIG. 12 shows a larger view of openings 1015, with SPR fiber 1030 extending so as to go through one of the openings 1015, similarly to FIG. 11. The portion of SPR fiber 1030 shown is inside the liner 1012, and exposed to direct plasma during operation of the substrate processing chamber. For ease of description and illustration, FIGS. 11 and 12 do not show the uncladded portions of the SPR fiber 1030 (or, in the case of FIG. 11, SPR fiber 1030').

In the case of a substrate processing chamber for dielectric etch, a shroud 1050 may surround liner 1012. In one aspect, the shroud 1050 is made of silicon. The ends of SPR fibers 1030, 1030' may extend through shroud 1050. In that event, instead of being inside liner 1012, the SPR fibers 1030, 1030' may remain outside the liner 1012, with the exposed (uncladded) portions of the SPR fibers 1030, 1030' aligning with one of the openings 1015. The portions of SPR fibers 1030, 1030' extending behind shroud 1050 may be inserted in silicon tubes to protect them from etchants in the substrate processing chamber.

Principles of operation of SPR fibers are well known, and for brevity of description will not be repeated here. By way of brief overview, looking more closely at the operation of the SPR fiber 600, because of the interface between the metal layer 610 and the dielectric material 620, a surface plasmon wave (SPW) will propagate along the interface. In one aspect, the SPW is a p-polarized electromagnetic wave. When that wave is incident on the metal-dielectric interface so that a propagation constant (and consequent energy) of a resulting evanescent wave (so-called because it decays exponentially with distance) equals that of the SPW, strong absorption of light will occur. The resulting output signal will dip substantially at a particular wavelength (the resonance wavelength). One way of expressing such a resonance condition is as follows:

$$K_0 n_c \sin\vartheta = K_0 \left( \frac{\varepsilon_{mr} n_s^2}{\varepsilon_{mr} + n_s^2} \right)^{1/2} ; K_0 = \frac{2\pi}{\lambda} \quad (1)$$

The term on the left-hand side of the above equation is the propagation constant ($K_{inc}$) of the evanescent wave generated as a result of Attenuated Total Reflection (ATR) of the light incident at an angle θ through a light coupling device (such as a prism or an optical fiber) of refractive index $n_c$. The right-hand term is the SPW propagation constant ($K_{SP}$), with $\varepsilon_{mr}$ as the real part of the metal dielectric constant ($\varepsilon_m$) and $n_s$ as the refractive index of the sensing (dielectric) layer.

In all of FIGS. 3-10, the SPR fibers are not drawn to scale. In particular, openings in the fibers, and diameters of the fibers, are not shown as being to scale. Wavelengths of light passed through the fiber, and formation of surface plasmon waves (SPW) and formation of evanescent waves in the vicinity of exposed portions of the fibers, will be a function of lengths of the openings and diameters of the fibers, in addition to the criteria described earlier.

Various classes of materials are known to have plasma resistant features or capabilities, including, for example, oxides and nitrides of various elements. Depending on the material buildup being monitored, and taking into account spectral properties of these plasma resistant materials, some such materials may be more suitable as coating for the SPR fiber than others. In one aspect, it is relevant to consider the type of material buildup being monitored. For example, oxides of silicon or chlorine, or fluorides of carbon, may build up on walls of a chemical etch (CE) chamber. Materials used for the insert in the exposed portion of the SPR fiber should have transmission spectra which are distinguishable from the spectrum of the material whose buildup is being monitored.

Taking the foregoing into account, Zirconium nitride (ZrN) is one plasma resistant material which may be used. There are others which meet the just-listed criteria.

Using an SPR fiber as a detector in a substrate processing chamber can provide several advantages. In no particular order, the advantages include the following. The structure can be simpler, and can use the same detection and processing circuitry and approach as in prior measurement techniques. Location of the fiber, and in particular the fiber opening, within the chamber is more flexible, subject only to the desirability of not affecting the processes being carried out within the chamber.

In addition, instead of having to deal with material buildups in multiple locations around the wall of the substrate processing chamber, only material buildup on the SPR fiber itself need be addressed. No estimations of buildups in multiple locations is necessary.

As noted earlier, in one aspect the input light may come from a QCL, and in another aspect the input light may come from a DFB laser. One aspect of QCL is that QCL can scan a large band, for example, from 5-12 um, covering a signature of multiple molecules in the infrared (IR) spectrum. This coverage goes hand in hand with IR detectors, which can cover relatively large bands in the IR domain. In comparison, a DFB laser addresses a much, much narrower band, of a wavenumber of one or less, meaning that use of a DFB laser will be confined primarily to detection of a single molecule.

Figure 13:
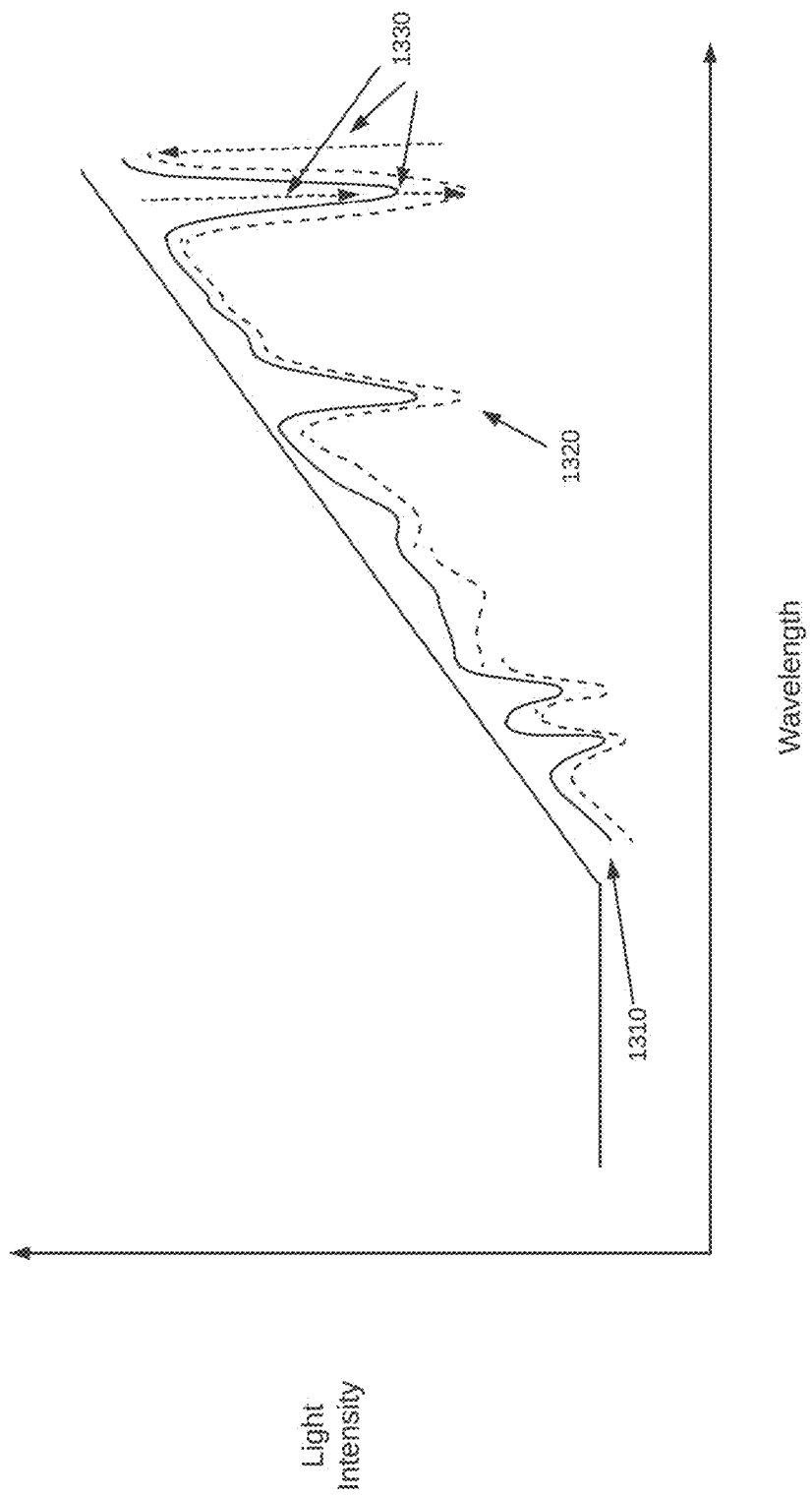
FIG. 13 is a graph of light intensity versus wavelength.

FIG. 13 shows a graph of light intensity versus wavelength. The solid straight lines depict a condition in which there is no laser emission, and so no absorption in the SPR fiber. The upwardly slanted solid line corresponds to a ramp from the beginning of a band to the end of the band. The solid curved line 1310 and the dashed curved line 1320 depict peaks or valleys which represent a signature of particular molecules. For example, during substrate processing, CF, $CF_x$, $SiCl_x$, $SiO_x$, $CH_x$, or OH (moisture) deposits may grow on the walls of a substrate processing chamber. The solid curved line 1310 may represent certain amounts of deposits, while the dashed curved line 1320 may represent different amounts of deposits, leading to different amplitudes of peaks or valleys. The dotted lines 1330 trace a deviation resulting from deposits on the chamber walls, followed by a return, after cleaning the walls, to a condition more nearly approximating clean chamber walls (i.e. absence of deposits).

In terms of detection of buildup on the uncladded portions of the SPR fiber, various known techniques may be used to obtain and process data that is generated as a result of transmission of light through the SPR fiber in the substrate processing chamber. In one aspect, individual measurements may be taken and analyzed to ascertain buildup thickness. The measurements may be taken in between operations of the substrate processing chamber. Those operations may or may not be at regular time intervals, but that is not critical to the efficacy of the detection system. Depending on the processes being used, and their duration, different amounts of buildup may result from different operations of the substrate processing system. In another aspect, multiple measurements may be taken at specific intervals, and those measurements integrated to ascertain buildup thickness, rate of buildup, or other parameters relevant to determination of a condition of walls of the substrate processing chamber.

In one aspect, as described above, an opening section of the SPR fiber may be approximately 1 cm. It is possible to optimize the size of the opening (making it either larger or smaller) to either increase or minimize the absorbance effective area. Also, as described above, it is possible to provide multiple openings in different areas of the chamber, again subject to the desirability of not affecting processes being carried out within the chamber. With known absorbance characteristics at each opening, and known characteristics of coatings over each opening, it is possible to observe conditions in different parts of the chamber while processes are being carried out.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A OR B OR C), using a non-exclusive logical OR, and should not be construed to mean "at least one of A, at least one of B, and at least one of C." It should be understood that one or more steps within a method may be executed in different order (or concurrently) without altering the principles of the present disclosure.

In some implementations, a controller is part of a system, which may be part of the above-described examples. Such systems can comprise semiconductor processing equipment, including a processing tool or tools, chamber or chambers, a platform or platforms for processing, and/or specific processing components (a wafer pedestal, a gas flow system, etc.). These systems may be integrated with electronics for controlling their operation before, during, and after processing of a semiconductor wafer or substrate. The electronics may be referred to as the "controller," which may control various components or subparts of the system or systems. The controller, depending on the processing requirements and/or the type of system, may be programmed to control any of the processes disclosed herein, including the delivery of processing gases, temperature settings (e.g., heating and/or cooling), pressure settings, vacuum settings, power settings, radio frequency (RF) generator settings, RF matching circuit settings, frequency settings, flow rate settings, fluid delivery settings, positional and operation settings, wafer transfers into and out of a tool and other transfer tools and/or load locks connected to or interfaced with a specific system.

Broadly speaking, the controller may be defined as electronics having various integrated circuits, logic, memory, and/or software that receive instructions, issue instructions, control operation, enable cleaning operations, enable endpoint measurements, and the like. The integrated circuits may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process on or for a semiconductor wafer or to a system. The operational parameters may, in some embodiments, be part of a recipe defined by process engineers to accomplish one or more processing steps during the fabrication of one or more layers, materials, metals, oxides, silicon, silicon dioxide, surfaces, circuits, and/or dies of a wafer.

The controller, in some implementations, may be a part of or coupled to a computer that is integrated with the system, coupled to the system, otherwise networked to the system, or a combination thereof. For example, the controller may be in the "cloud" or all or a part of a fab host computer system, which can allow for remote access of the wafer processing. The computer may enable remote access to the system to monitor current progress of fabrication operations, examine a history of past fabrication operations, examine trends or performance metrics from a plurality of fabrication operations, to change parameters of current processing, to set processing steps to follow a current processing, or to start a new process. In some examples, a remote computer (e.g. a server) can provide process recipes to a system over a network, which may include a local network or the Internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations. It should be understood that the parameters may be specific to the type of process to be performed and the type of tool that the controller is configured to interface with or control. Thus as described above, the controller may be distributed, such as by comprising one or more discrete controllers that are networked together and working towards a common purpose, such as the processes and controls described herein. An example of a distributed controller for such purposes would be one or more integrated circuits on a chamber in communication with one or more integrated circuits located remotely (such as at the platform level or as part of a remote computer) that combine to control a process on the chamber.

Without limitation, example systems may include a plasma etch chamber or module, a deposition chamber or module, a spin-rinse chamber or module, a metal plating chamber or module, a clean chamber or module, a bevel edge etch chamber or module, a physical vapor deposition (PVD) chamber or module, a chemical vapor deposition (CVD) chamber or module, an atomic layer deposition (ALD) chamber or module, an atomic layer etch (ALE) chamber or module, an ion implantation chamber or module, a track chamber or module, and any other semiconductor processing systems that may be associated or used in the fabrication and/or manufacturing of semiconductor wafers.

As noted above, depending on the process step or steps to be performed by the tool, the controller might communicate with one or more of other tool circuits or modules, other tool components, cluster tools, other tool interfaces, adjacent tools, neighboring tools, tools located throughout a factory, a main computer, another controller, or tools used in material transport that bring containers of wafers to and from tool locations and/or load ports in a semiconductor manufacturing factory.

What is claimed is:

1. A substrate processing system comprising:
a processing chamber having a chamber wall;
a pedestal arranged in the processing chamber to hold a substrate for processing;
a showerhead arranged in the processing chamber to distribute plasma in the processing chamber; and
a detector system configured to detect a condition of the chamber wall, the detector system comprising:
a first surface plasmon resonance (SPR) fiber having a first end and a second end positioned outside the processing chamber, and an inner portion of the first SPR fiber positioned inside the processing chamber;
a light source providing light as first input light to the first end of the first SPR fiber; and
a controller configured to control an amount of light provided to the first end of the first SPR fiber, and to receive light at the second end of the first SPR fiber as first output light, the controller analyzing the first input light and the first output light to determine the condition of the chamber wall.

2. The substrate processing system of claim 1, wherein the processing chamber further includes a first feedthrough; and wherein the first and second ends of the first SPR fiber extend through the first feedthrough.

3. The substrate processing system of claim 2, wherein the processing chamber further includes a second feedthrough, and the first end of the first SPR fiber extends through the first feedthrough, and the second end of the first SPR fiber extends through the second feedthrough.

4. The substrate processing system of claim 3, wherein the first and second feedthroughs are proximate each other on one side of the processing chamber.

5. The substrate processing system of claim 3, wherein the first and second feedthroughs are on opposite sides of the processing chamber.

6. The substrate processing system of claim 1, wherein the first SPR fiber comprises a first central optical fiber with first cladding surrounding the first central optical fiber, the first cladding having a first opening positioned so that the first opening is inside the processing chamber, the first SPR fiber further comprising, within the first opening:
a first metal film disposed over the first central optical fiber; and
a first layer of plasma resistant material disposed over the first metal film.

7. The substrate processing system of claim 6, wherein the plasma resistant material comprises a material selected from the group consisting of nitrides and oxides of zirconium and yttrium.

8. The substrate processing system of claim 6, wherein the first cladding has a second opening positioned inside the processing chamber, the first SPR fiber further comprising, within the second opening:
a second metal film disposed over the first central optical fiber; and
a second layer of plasma resistant material disposed over the second metal film.

9. The substrate processing system of claim 3, wherein the processing chamber further includes third and fourth feedthroughs, the detector system further comprising a second SPR fiber having a first end and a second end positioned outside the processing chamber, and an inner portion of the second SPR fiber positioned inside the processing chamber, on an opposite side of the processing chamber from the first SPR fiber;
the light source providing light as second input light to the first end of the second SPR fiber; and
the controller configured to control an amount of light provided to the first end of the second SPR fiber, and to receive light at the second end of the second SPR fiber as second output light, the controller analyzing the second input light and the second output light to determine the condition of the chamber wall.

10. The substrate processing system of claim 9, wherein the second SPR fiber comprises a second central optical fiber with second cladding surrounding the second central optical fiber, the second cladding having a third opening positioned so that the third opening is inside the processing chamber, the second SPR fiber further comprising, within the third opening:
a third metal film disposed over the second central optical fiber; and
a third layer of plasma resistant material disposed over the third metal film.

11. The substrate processing system of claim 10, wherein the second cladding has a fourth opening positioned inside the processing chamber, the second SPR fiber further comprising, within the fourth opening:
a fourth metal film disposed over the second central optical fiber; and
a fourth layer of plasma resistant material disposed over the fourth metal film.

12. The substrate processing system of claim 3, the detector system further comprising:
a reference surface plasmon resonance (SPR) fiber having first and second ends and positioned outside the processing chamber;
the light source providing light as reference input light to the first end of the reference SPR fiber; and
the controller configured to control an amount of light provided to the first end of the reference SPR fiber, and to receive light at the second end of the reference SPR fiber as reference output light, the controller to compare the reference output light to the first output light to determine a baseline for ascertaining the condition of the chamber wall.

13. The substrate processing system of claim 12, the controller to compare the reference output light to the first output light after the processing chamber wall has been cleaned, and before subsequent use of the substrate processing system.

14. In a substrate processing system comprising a processing chamber having a chamber wall and at least one feedthrough, a pedestal arranged in the processing chamber to hold a substrate for processing, and a showerhead arranged in the processing chamber to distribute plasma in the processing chamber;
 a detector system configured to detect a condition of the chamber wall, the detector system comprising:
  a first surface plasmon resonance (SPR) fiber having a first end and a second end positioned outside the processing chamber, and an inner portion of the first SPR fiber positioned inside the processing chamber;
  a light source providing light as first input light to the first end of the first SPR fiber; and
  a controller configured to control an amount of light provided to the first end of the first SPR fiber, and to receive light at the second end of the first SPR fiber as first output light, the controller analyzing the first input light and the first output light to determine the condition of the chamber wall.

15. The detector system of claim 1, wherein the first SPR fiber comprises a first central optical fiber with first cladding surrounding the first central optical fiber, the first cladding having a first opening positioned so that the first opening is inside the processing chamber, the first SPR fiber further comprising, within the first opening:
 a first metal film disposed over the first central optical fiber; and
 a first layer of plasma resistant material disposed over the first metal film.

16. The detector system of claim 15, wherein the first cladding has a second opening positioned inside the processing chamber, the first SPR fiber further comprising, within the second opening:
 a second metal film disposed over the first central optical fiber; and
 a second layer of plasma resistant material disposed over the second metal film.

17. The detector system of claim 14, further comprising a second SPR fiber having a first end and a second end positioned outside the processing chamber, and an inner portion of the second SPR fiber positioned inside the processing chamber, on an opposite side of the processing chamber from the first SPR fiber;
 the light source providing light as second input light to the first end of the second SPR fiber; and
 the controller configured to control an amount of light provided to the first end of the second SPR fiber, and to receive light at the second end of the second SPR fiber as second output light, the controller analyzing the second input light and the second output light to determine the condition of the chamber wall.

18. The detector system of claim 17, wherein the second SPR fiber comprises a second central optical fiber with second cladding surrounding the second central optical fiber, the second cladding having a third opening positioned so that the third opening is inside the processing chamber, the second SPR fiber further comprising, within the third opening:
 a third metal film disposed over the second central optical fiber; and
 a third layer of plasma resistant material disposed over the third metal film.

19. The detector system of claim 18, wherein the second cladding has a fourth opening positioned inside the processing chamber, the second SPR fiber further comprising, within the fourth opening:
 a fourth metal film disposed over the second central optical fiber; and
 a fourth layer of plasma resistant material disposed over the fourth metal film.

20. The detector system of claim 14, the detector system further comprising:
 a reference surface plasmon resonance (SPR) fiber having first and second ends and positioned outside the processing chamber;
 the light source providing light as reference input light to the first end of the reference SPR fiber; and
 the controller configured to control an amount of light provided to the first end of the reference SPR fiber, and to receive light at the second end of the reference SPR fiber as reference output light, the controller to compare the reference output light to the first output light to determine a baseline for ascertaining the condition of the chamber wall.

21. The detector system of claim 20, the controller to compare the reference output light to the first output light after the processing chamber wall has been cleaned, and before subsequent use of the substrate processing system.

* * * * *